United States Patent [19]

Tomita et al.

[11] 4,104,527

[45] Aug. 1, 1978

[54] SCANNING APPARATUS FOR CROSS-SECTIONAL INSPECTION EQUIPMENT

[75] Inventors: Chuji Tomita, Tokyo; Hiroshi Abe, Kashiwa, both of Japan

[73] Assignee: Hitachi Medical Corporation, Tokyo, Japan

[21] Appl. No.: 727,866

[22] Filed: Sep. 29, 1976

[30] Foreign Application Priority Data

Sep. 30, 1975 [JP] Japan .................................. 50/117122

[51] Int. Cl.² ............................................ G03B 41/16
[52] U.S. Cl. ................................. 250/445 T; 250/490
[58] Field of Search ............... 250/445 R, 445 T, 446, 250/447, 448, 490, 523, 525

[56] References Cited

U.S. PATENT DOCUMENTS 3,986,031  10/1976  Chekroun .................. 250/445 T

*Primary Examiner*—Craig E. Church

[57] ABSTRACT

A scanning apparatus for cross-sectional inspection equipment in which an X-ray source and a detector, which are arranged facing each other with an object in between, reciprocate along and rotate about a required cross-sectional plane of the object. The X-ray source and detector are mounted on a movable frame which is provided on a rotating disc and reciprocate, after being rotated through a small rotating-angle of the rotating disc by means of one drive source and mechanical mechanism. Thus, accurate operating timing and simplified construction are achieved.

8 Claims, 7 Drawing Figures

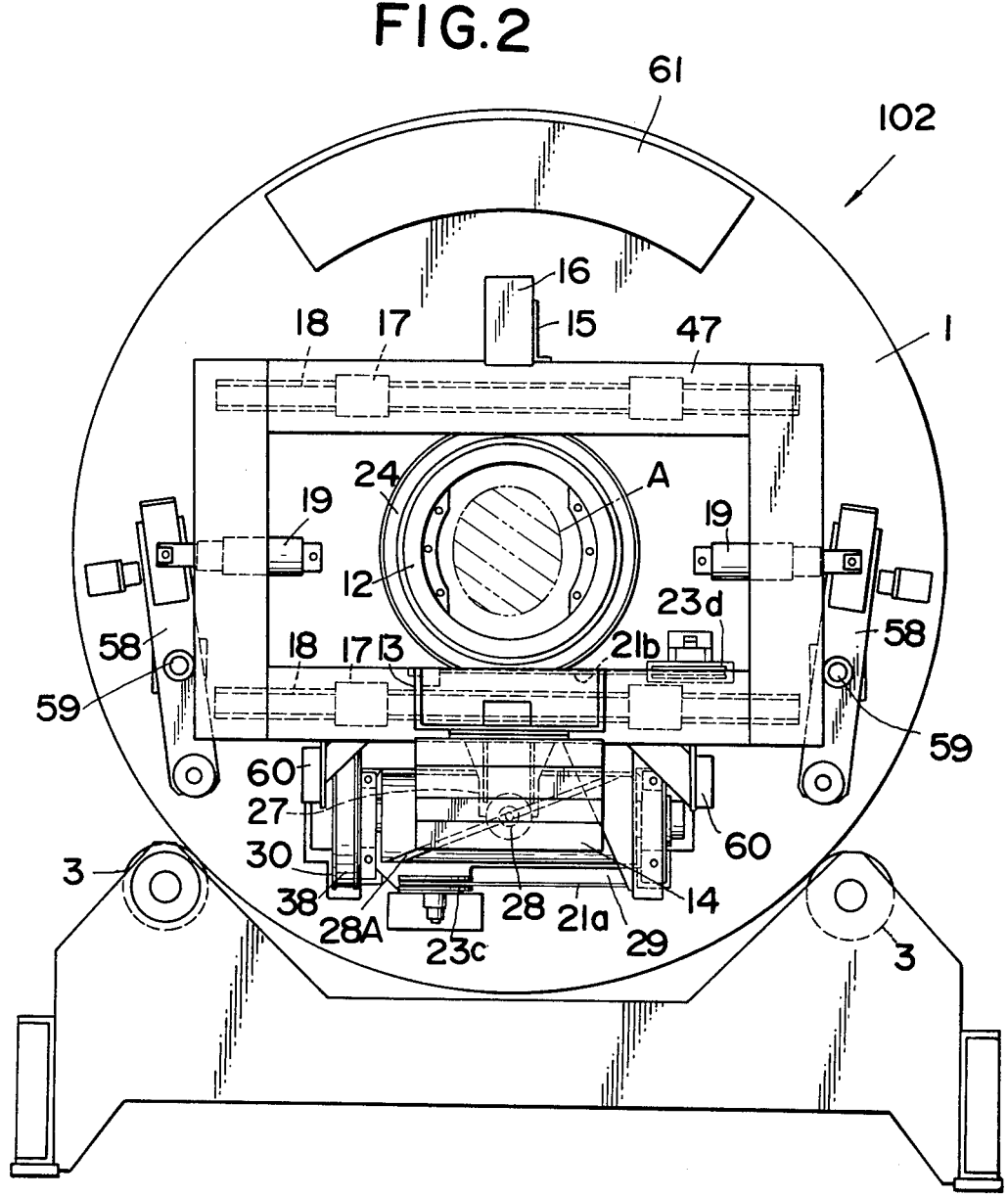

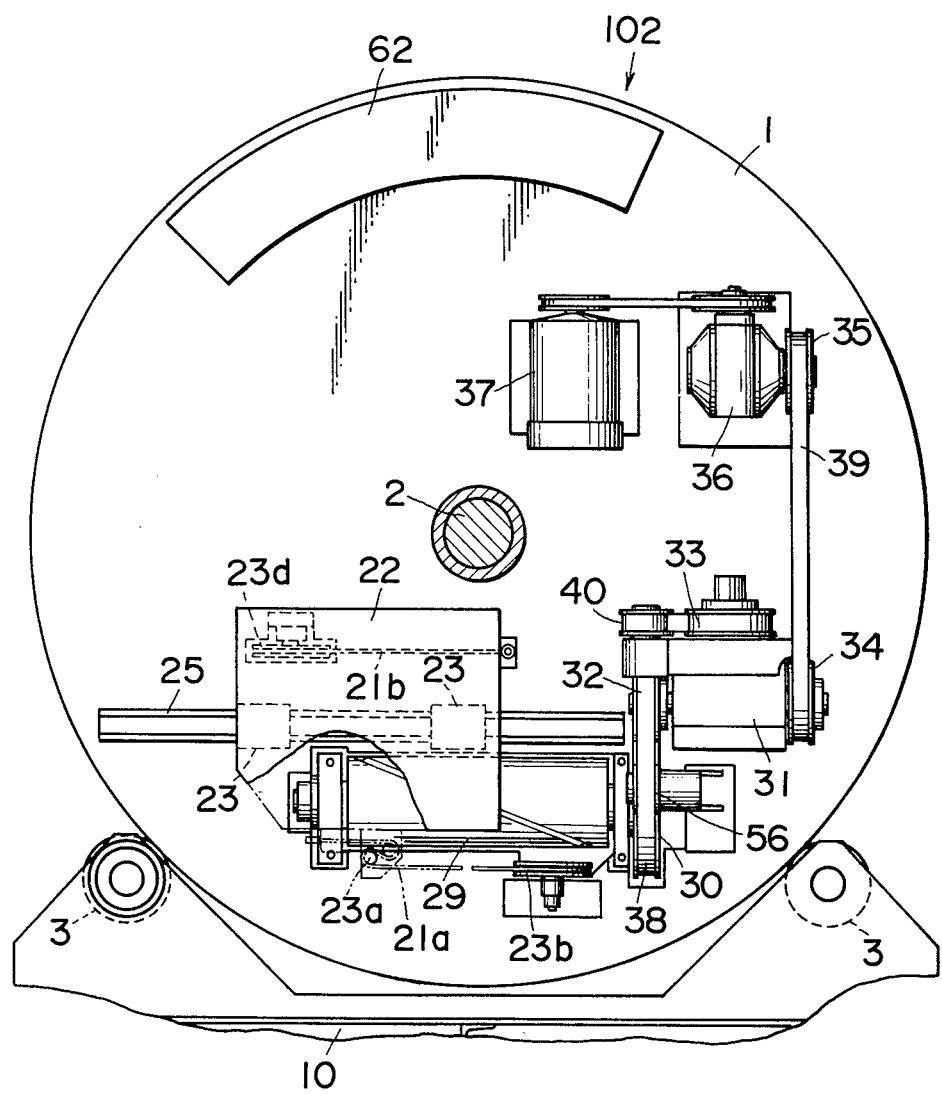

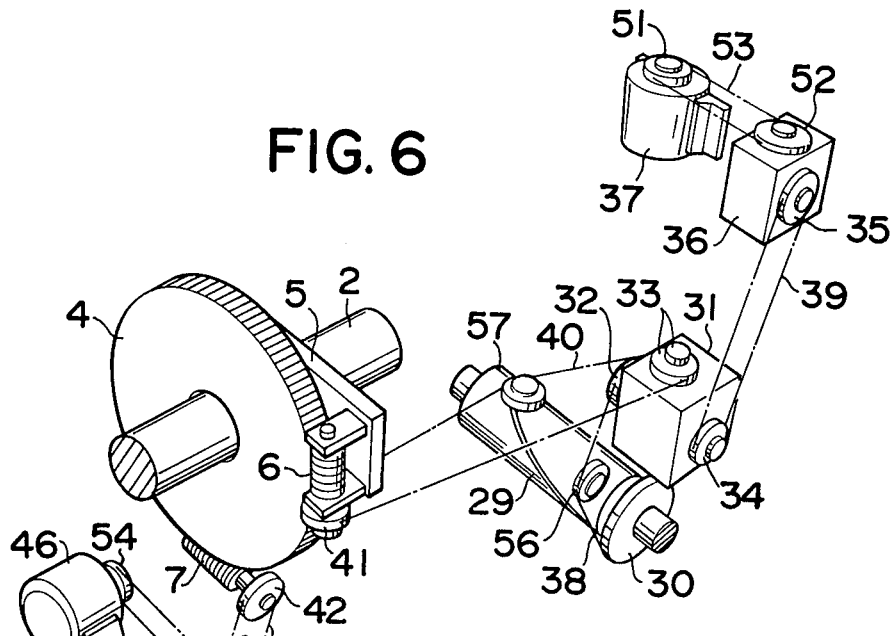
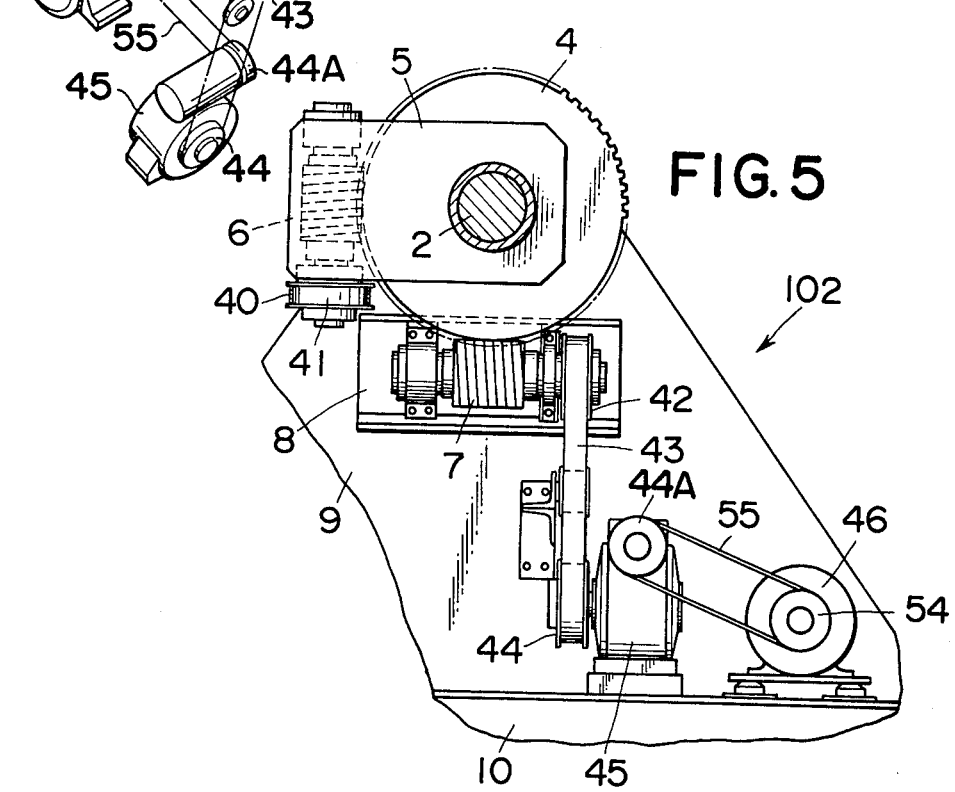

SCANNING APPARATUS FOR CROSS-SECTIONAL INSPECTION EQUIPMENT

BACKGROUND OF THE INVENTION

The present invention relates to a scanning apparatus for cross-sectional inspection equipment and more particularly to a scanning apparatus in which an X-ray source and a detector, which are arranged facing each other with an object to be inspected in between, reciprocate along and rotate about a required cross-sectional inspection plane of the object.

In general, this type of equipment comprises a scanning apparatus and an image processing apparatus including a computer. The scanning apparatus has an X-ray source and a detector which are positioned facing each other with the object in between. The X-ray source and detector are arranged so that they both travel parallel to the required cross-sectional plane of the object to be inspected for scanning, and in turn both are rotated through a small angle and then caused to travel again for scanning, and these steps are repeated. Generally, parallel scanning is performed after each rotation of one degree from 0° to 180°. The detector collects data in the form of X-ray beams and transmits it to the computer built in the image processing apparatus on which the data is displayed as the cross-sectional image of the object. This type of inspection equipment is already known — for example, Japanese Patent Application No. Sho 49-47032 (Publicized Patent No. Sho 50-28385, Publication Date — Mar. 22, 1975) which is based on British patent application Nos. 19528/73, 38817/33, 39070/73, 39420/73 and 47507/73.

Such prior art inspection equipment is composed of a rotating disc, an object-supporting means provided at the center of rotation of the rotating disc, and a movable bar on which the X-ray source and detector, both being mounted on the rotating disc, travel parallel to the required cross-sectional plane of the object to be inspected. The rotating disc is rotated through a small angle — for instance: 1° — each time the movable bar travels. The movable bar is driven by a motor and an endless belt, and the rotating disc is driven by a separate motor the rotation of which is synchronized with the movement of the movable bar.

BRIEF SUMMARY OF THE INVENTION

It is an object of the invention to provide a scanning apparatus in which an X-ray source and a detector travel in parallel for scanning and rotate with accurate operating timing and in smooth manner, featuring simplified construction and low cost.

It is another object of the invention to provide a scanning apparatus in which parallel scanning and rotation are carried out by a single drive source, and more particularly parallel scanning and rotation of the X-ray source and detector are all carried out mechanically, whereby maintenance, inspection and repair of the apparatus can be carried out by an engineer who is not specially trained.

It is another object of the invention to provide a scanning apparatus which provides smooth operation and high reliability by minimizing impacts caused during operation.

Other objects of the invention will become apparent from the following description of a preferred embodiment with reference to the accompanying drawings.

BRIEF DESCRIPTION OF THE DRAWINGS

The accompanying drawings show one form of scanning apparatus embodying the invention, in which

FIG. 2 is an elevational view of the scanning apparatus of FIG. 1, with the outer casing thereof;

FIG. 4 is a vertical section of the scanning apparatus taken along line IV — IV in FIG. 3;

FIG. 5 is a vertical section of the scanning apparatus taken along line V — V in FIG. 3;

FIG. 6 is a schematic illustration of a drive system for the scanning apparatus.

DETAILED DESCRIPTION OF THE INVENTION

Figure 1:
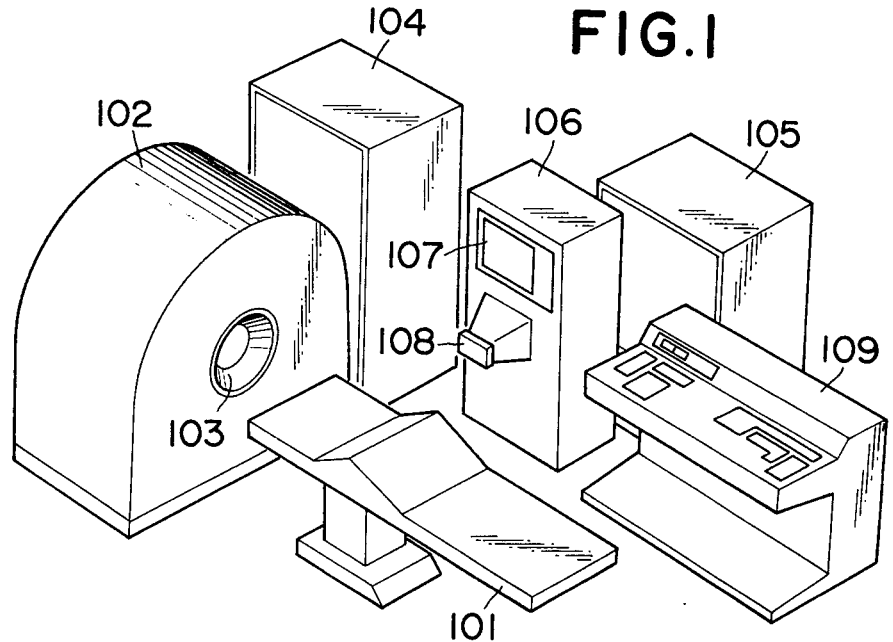
FIG. 1 is an external perspective view of an embodiment of the invention with other devices constituting inspection equipment.

Referring now to FIG. 1, there is illustrated the overall setup of the cross-sectional inspection equipment of the present invention, which is arranged for the cross-sectional inspection of a head of a human being. An object to be inspected rests on a movable bed 101, and the head of the object is securely held on the movable bed and inserted into an opening 103 of a scanning apparatus 102. X-rays are produced from an X-ray tube in the scanning apparatus by means of an X-ray generator 104, pass through the object and then reach a detector in the scanning apparatus. Detected signals are finally transmitted to a computer 105. The detected signals are processed by the computer and then the image of the required cross-sectional plane of the object is displayed on a monitor television 107 of a displaying unit 106. This displayed image can be recorded by a camera 108 attached to the displaying unit. Each device or unit can be operated and controlled by a control cabinet 109.

As described above, the present invention relates to the scanning apparatus for foregoing inspection equipment. FIG. 2 to FIG. 5, inclusive, show the scanning apparatus with the outer casing removed. The outer casing 110 is illustrated in phantom lines in FIG. 3.

A rotating disc 1 is circular in form. A shaft 2 has one end which is coaxially fixed to the center of the rotating disc. The opposite end of the shaft is supported by a bearing attached to a supporting plate 9 on a bed 10. The periphery of the rotating disc rests on rollers 3 which are rotatably secured to the bed 10. As a result, the rotating disc can rotate about the center of the shaft 2 above the bed 10. Counterweights 61 and 62 are provided on both sides of the rotating disc so that the rotating disc can rotate smoothly and avoid imbalance caused by devices thereon which are mentioned later. One of rollers 3 is provided with a brake 3a which is actuated or released in response to the switching of the direction of movement of a movable frame 47 described later. On the opposite surface of the rotating disc is provided a housing for accommodating the object. The housing comprises an inner cylinder 12 and an outer cylinder 24. The inner cylinder 12 is fixedly secured to the outer casing 110 while the outer cylinder 24 is flanged to the rotating disc. A bearing is provided between the two cylinders so that the outer cylinder can rotate with the rotating disc. Furthermore, in the vicinity of the inlet of each cylinder are provided rings 12a and 24a made of materials through which X-rays will easily pass, such as acryl resin.

The movable frame 47 is rectangular in form, and the bars thereof are attached to the rotating disc in such manner that the frame 47 surrounds the outer cylinder 24. A sliding saddle 17 is fixed to each of the upper and lower bars of the movable frame. Two guide rails 18 are mounted on the disc 1 above and below outer cylinder 24, and the sliding saddles 17 are slidably mounted on the rails 18. An X-ray source, in this case an X-ray tube 14, is supported by an arm 13 extending from the lower bar of the movable frame, and a detector 16 is supported by an arm 15 extending from the upper bar of the movable frame. An X-ray emission opening of the X-ray tube is directed toward the detector so that the detector can receive X-ray beams from the X-ray tube. Therefore, the object is accommodated in the inner cylinder 12 and the movable frame travels on the rail, so that the X-ray tube and the detector move along the cross-sectional plane of the object, so that the detector can receive X-ray beams passing through rings 12a and 24a of the inner and outer cylinders. Of course, it is recommended that the distance of travel of the movable frame be longer than the length of the cross-sectional plane of the object.

As shown in FIGS. 2-6, in the scanning apparatus of the present invention, a motor 37 mounted on disc 1 drives an intermittent transmission gear 31, also mounted on disc 1, which in turn rotates a barrel cam 29 which causes the movable frame travel. At the same time, the shaft 2 is turned at a slight angle by means of a worm 6 and a worm gear 4 when the travel direction of the movable frame is switched.

Hereinafter, detailed description of the drive means is given. An arm 27 is provided on the lower bar of the movable frame, and a pin 28 located at tip of the arm 27 is engaged in a cam groove 28A of the barrel cam 29. The cam groove is shaped so that the movable frame travels on the guide rail and reciprocates one stroke for each rotation of the barrel cam. The barrel cam itself is positioned in an opening in the rotating disc and a shaft extending from the barrel cam is supported by the rotating disc via a bearing. A pulley 30 is fixedly secured on the shaft of the barrel cam and is connected with a pulley 32 of the intermittent transmission gear 31 through a belt 38.

The intermittent transmission gear is a well-known type comprising a special cylindrical cam and a turret having the pin engaged with the groove of the special cylindrical cam. Pulleys 32 and 34 are fixedly secured on a driving shaft extending from the cam, and a pulley 33 is fixedly secured to an intermittently driven shaft extending from the turret. As stated earlier, the pulley 32 is engaged with the pulley 30 through a belt 38, and the pulley 33 is engaged with a pulley 41 of the worm 6 through a belt 40. The belts 38 and 40 are provided with tension pulleys 56 and 57, respectively. More specifically, the tension pulley 56 is supported by an arm extending from the back of the rotating disc and the tension pulley 57 is supported by an arm extending from the casing of the intermittent transmission gear, respectively.

The worm 6 is supported by a member 5 fixed on the shaft 2 via a bearing. The worm gear 4 enmeshed with the worm 6 is mounted on the shaft 2 in a loose fit or via a bearing. A further worm 7 is enmeshed with the worm gear in order to prevent the rotation of the worm gear as explained below. Therefore, when only the worm 6 is rotated, the worm 6 is moved around the worm gear, maintaining its engagement with worm gear 4, so that the shaft 2 is rotated. On the contrary, when only the worm 7 is rotated, both the worm gear and worm 6 start to rotate, which causes the shaft to rotate.

Figure 7:
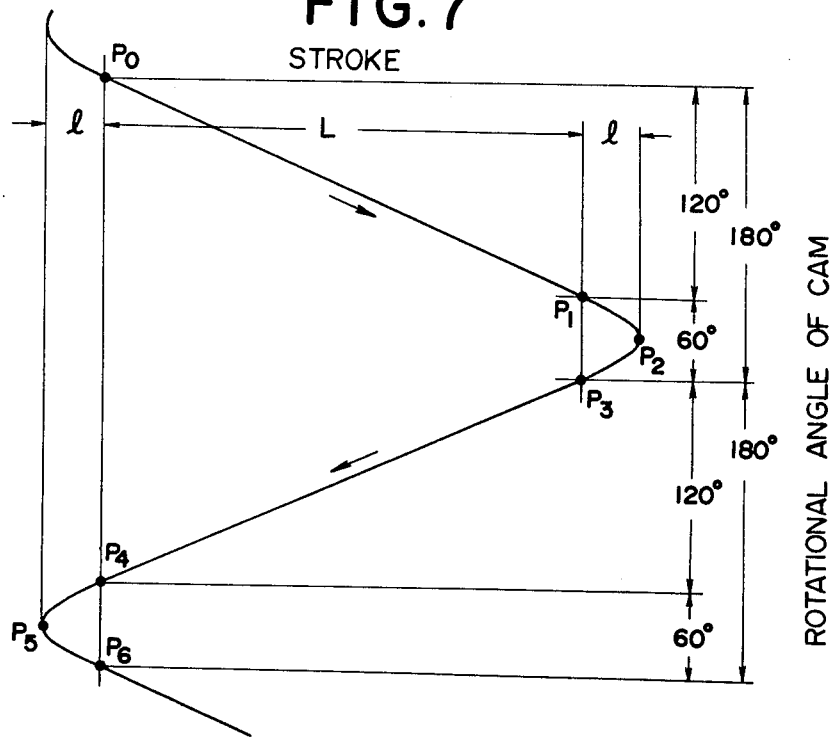
FIG. 7 is a cam diagram of a barrel cam for the scanning apparatus.
Figure 3:
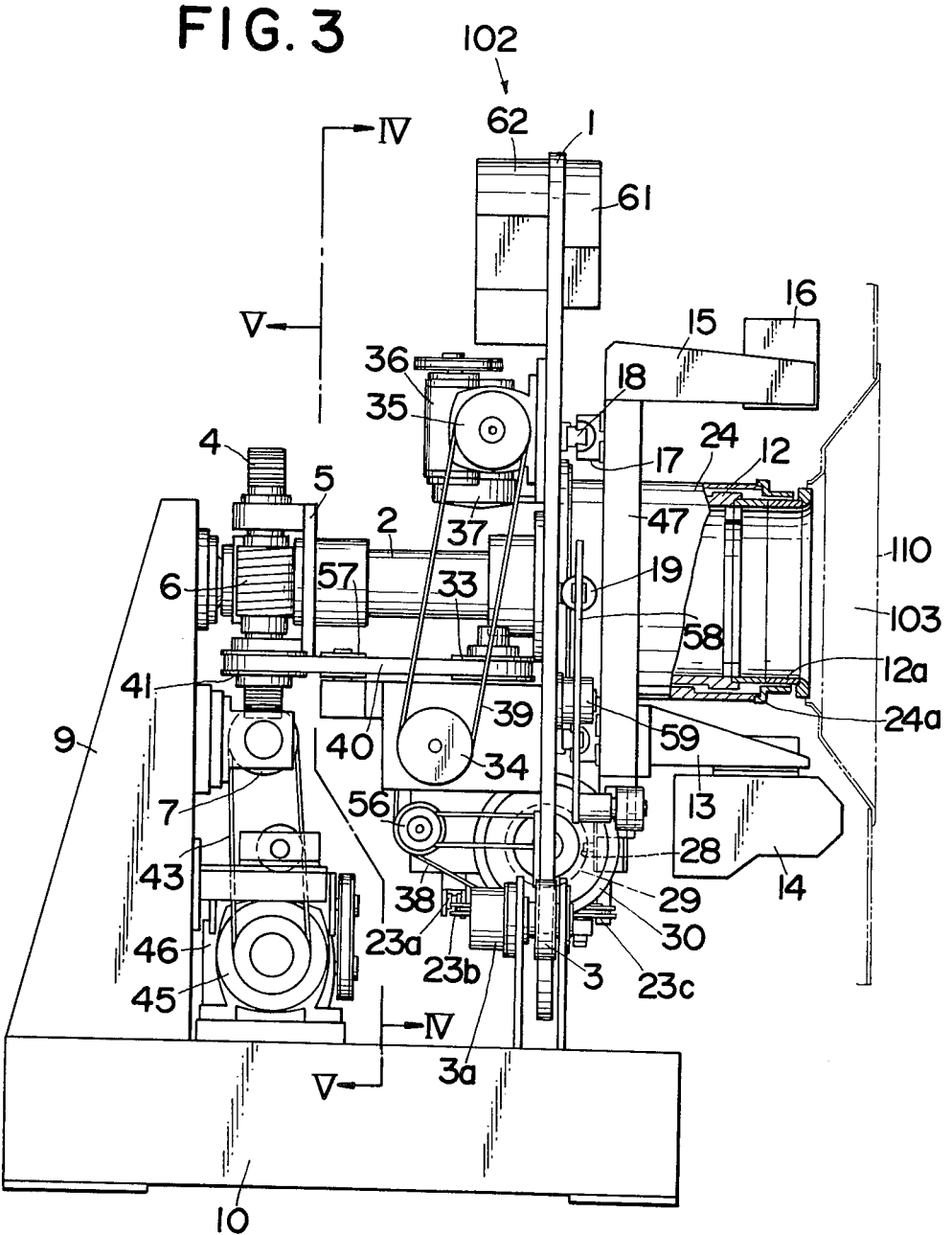
FIG. 3 is a left side view of FIG. 2.

The motor 37 and a reduction gear 36 provided on the rotating disc 1 are connected with each other through pulleys 51 and 52 and a belt 53. The pulley 35 mounted on the output shaft of the reduction gear is engaged with a pulley 34 on an driving shaft of the intermittent transmission gear through a belt 39. Accordingly, the rotation of the motor is transmitted to the driving shaft of the intermittent transmission gear 31 through the reduction gear 35. Thereby, the barrel cam 29 is continuously rotated to reciprocate the movable frame 47. On the other hand, the driven shaft of the intermittent transmission gear 31 is intermittently turned at reduced speed relative to the rotation of the motor shaft in order to rotate the worm 6 and thus rotate the rotating disc through the shaft 2. The driven shaft is driven so that it rotates when the direction of travel of the movable frame 47 is reversed by the barrel cam 29, so that both the X-ray tube and detector are rotated through a small angle when travel in one direction or return travel of the movable frame is completed. The barrel cam 29, as explained above, has the cam groove 28A shaped for causing the movable frame to reciprocate one stroke for each rotation of the barrel cam. As illustrated in FIG. 7, the cam groove is composed of straight lines $P_0$-$P_1$ and $P_3$-$P_4$, and sine curves $P_1$-$P_3$ and $P_4$-$P_5$ which are positioned on the cylindrical surface of the barrel cam. Hence, the cam groove length $L + l$ is equal to the stroke of the movable frame, which is of course longer than the length of the cross-sectional plane of the object.

The ratio between the rotation of the pulley 32 on the driving shaft of the intermittent transmission gear and the pulley 30 of the barrel cam is made 2:1. In short, when the pulley 32 rotates one turn, the barrel cam is rotated a half turn. More specifically, when the pulley 32 is rotated one turn, the movable frame travels $L + 2l$ corresponding to the straight line $P_0$-$P_1$ and the curve $P_1$-$P_3$. In addition, when the pulley 32 is rotated one more turn, the movable frame in turn travels in the reverse direction $L + 2l$ corresponding to the straight line $P_3$-$P_4$ and the curve $P_4$-$P_6$. During each stroke, the speed of the movable frame is reduced at curves $P_1$-$P_2$ and $P_4$-$P_5$, and accelerated at curves $P_2$-$P_3$ and $P_5$-$P_6$.

In the intermittent transmission gear 31, when the driving shaft rotates one turn, the driven shaft remains stopping during ⅚ of the rotation of the driving shaft and in turn rotates 1/6 turn during the remaining ⅙ rotation thereof. Furthermore, the driven shaft is arranged to be rotated at curves $P_1$-$P_3$ and $P_4$-$P_6$ of the cam groove of the barrel cam. Therefore, during the change of direction of the travel of the movable frame, the worm 6 starts to rotate by means of pulleys 33 and 41 and the belt 40 and the rotating disc is also rotated through the shaft 2.

The worm 6 is single threaded and the worm gear has 60 teeth. Thereby, when the direction of travel of the movable frame is switched, the worm gear 4 is rotated 1/360 turn (1/6 × 1/60 = 1/360). However, since the worm gear is locked by the worm 7 as described earlier, the worm 6 moves around the worm gear 1/360 turn thereof with the engagement between the worm 6 and worm gear 4 being maintained. As a result, the shaft 2 and hence the rotating disc rotates through angle of 1°. By repeating the aforesaid steps, the X-ray source and detector reciprocate along the cross-sectional plane of the object at each 1° from 0° to 180°.

In the apparatus of the present invention, to obtain accurate syncronous timing of the actions described above, a special belt provided with shallow grooves at a certain pitch, known as a timing belt, and a special pulley having concave and convex surfaces matched to the timing belt surface are employed for belts 39, 40 and 53 and the pulleys engaged therewith.

Moreover, in the scanning apparatus of the present invention, to smoothly switch the direction of travel of the movable frame, the rotating disc is provided with dampers 19. These dampers are of a well known construction have a piston and coil spring contained in a casing with the end is pin connected to the rotating disc. In addition, the piston is pivotally connected to an end of a rocker arm 58 pivoted on shaft 59 on the rotating disc. The opposite end of the rocker arm 58 comes in contact with a stop 60 attached to an arm extending from the lower bar of the movable frame 47 when the movable frame is at the position determined by curves $P_1 - P_3$ and $P_4 - P_6$ of the cam groove of the barrel cam. After that, the rocker arm is rotated about a shaft 59. Accordingly, when the movable frame arrives at curves $P_1 - P_2$ and $P_4 - P_5$ of the cam groove, the speed of the movable frame is sufficiently reduced to allow switching the direction of travel thereof with a minimum shock.

In addition, at curves $P_2 - P_3$ and $P_5 - P_6$, the speed of the movable frame is rapidly increased by means of the returning force of the coil spring in the damper, so that the movable frame can travel at the same speed at curves $P_0 - P_1$ and $P_4 - P_6$.

What is more, in the scanning apparatus of the present invention, even when the rotating disc rotates, the movable frame will travels smoothly due to a counterweight 22 which is provided on the back side of the rotating disc (see FIG. 4). The counterweight 22 is provided with a sliding saddle 23 which is engaged with a guide rail 25 fixed to the rotating disc. One end of a rope 21a is fixed to the counterweight. This rope 21a passes around a roller 23a supported by an arm which extends downwardly from the counterweight, arrives at the front side of the rotating disc after passing around pulleys 23b and 23c both being supported by the rotating disc, and finally fixed to an arm which extends downwardly from the movable frame. One end of a rope 21b is fixed to the lower bar of the movable frame, and the opposite end thereof is fixed to the counterweight after passing around pulleys 23d supported by the rotating disc and extending along the back of the rotating disc.

Hereinafter, the operation of the apparatus is described. An object A will be positioned in the inner cylinder 12 so that the required cross-sectional inspection plane of the object A is parallel to the travel of the X-ray source 14 and the detector 16. When the motor 37 starts, the brake 3a is actuated to lock the roller 3. At the same time, the barrel cam 29 is rotated via the intermittent transmission gear 31, whereby the movable frame 47 is reciprocated in order to move the X-ray source and detector along the cross-sectional inspection plane of the object.

When the movable frame arrives at one end of the travel stroke, the locking of the roller 3 is released, and the worm 6 is rotated via the intermittent transmission gear. At this time, because the worm gear 4 is locked, the worm 6 moves around the worm gear, remaining in engagement therewith, whereby both the X-ray source and detector are rotated 1° via the frame 5 and shaft 2. With the disc 1 in the new angular position, the movable frame returns to its original position causing both the X-ray source and detector to travel herewith. After that, the rotating plate again turned at 1°, and the X-ray source and detector are caused to traveled again. This step is repeated at each 1° increment of rotation through 180°. By the aforesaid scanning, the detector can obtain X-ray absorption data on the required cross-sectional inspection plane of the object which in turn is transmitted to the image processing unit in order to display an image thereof. A detailed description of the image processing unit is omitted because it lies outside the scope of the present invention.

After the X-ray tube and detector are caused to scan at each 1° of rotation for 180°, they should be quickly returned to the starting position. FIG. 5 shows means for achieving the quick return. This means comprises the worm gear 4 and the further worm 7 engaged therewith. The worm 7 is, via a bearing, supported by a base plate 8 on a frame 9 extending from the bed 10. A pulley 42 and the worm 7 are mounted on the same shaft. Furthermore, the pulley 42 is, through a belt 43, engaged with a pulley 44a mounted on an output shaft of a reduction gear 45 fixed on the bed 10. An input shaft of the reduction gear 45 is also engaged with a shaft of a motor 46 fixed on the bed 10 through pulleys 44a and 54 and a belt 55. After the rotating disc has been rotated 180° by the motor 37, the motor 37 is stopped and at the same time the motor 46 is started by a limit switch (not shown) so as to rotate the worm 7. Thereby, the worm gear 4 is rotated with the worm 6 engaged therewith, which results in the reverse rotation of the rotating disc 1. When the rotating disc has reached the starting position, the motor 46 is stopped by the limit switch (not shown). The motor 46 includes a brake which prevents the rotation of the worm gear under normal conditions.

What is claimed is:

1. A scanning apparatus for cross-sectional inspection equipment, comprising a bed, rollers on said bed, a circular rotating disc having the periphery thereof rotatably supported on said rollers, a shaft rotatably mounted on said bed and on which said disc is mounted for rotation therewith, a housing positioned on the axis of rotation at the center of said rotating disc for accommodating therein an object to be inspected, a movable frame surrounding said housing, guide rails on said rotating disc on which said movable frame is mounted for travel along a required cross-sectional inspection plane of the object, an X-ray source and a detector mounted on said movable frame in positions opposed to each other with said housing therebetween, and drive means for driving said movable frame reciprocally along said rails and rotating said rotating disc in accordance with the travel of said movable frame, said drive means having a single driving source, an intermittent transmission gear on said disc and driven by said driving source, a barrel cam rotatably mounted on said rotating disc and driven for constant rotation from said drive source and having a cam groove with which said movable frame is engaged for driving said movable frame reciprocally along said guide rails, a worm rotatable around its own axis and fixed to said shaft for rotation around said shaft with the axis of rotation of the worm transverse to the axis of the shaft, said worm being rotated by the intermittent transmission gear, a worm gear loosely mounted on said shaft and meshing with said worm, and means engaged with said worm gear for blocking rotation of said worm gear relative to said shaft, said intermittent transmission gear driving said worm for rotating said disc a small amount when the direction of travel of said movable frame is reversed by said barrel cam.

2. A scanning apparatus according to claim 1, further comprising a damping means on said disc for damping the movement of said movable frame at the end of the travel therein in both directions.

3. A scanning apparatus according to claim 2, in which said damping means has a damper including a coil spring, a piston and a housing in which said coil spring and piston are housed, and a rocker arm rotatably secured to said rotating disc, said housing of damper being pivotally connected to said rotating disc, said piston being pivotally connected to one end of said rocker arm and the other end of said rocker arm being engaged by said movable frame at said end of reciprocating travel thereof.

4. A scanning apparatus according to claim 1, further comprising counterweights movably mounted on said disc and connected to said movable frame for counterbalancing the weight of said movable frame when the disc is positioned with the movable frame moving vertically.

5. A scanning apparatus according to claim 4, further comprising ropes connecting said counterweights and said movable frame, and a guide means attached to said rotating disc for guiding said ropes to between said movable frame and said counterweights.

6. A scanning apparatus according to claim 1, in which said barrel cam has a cam groove for causing said movable frame to travel through one reciprocating stroke for each rotation thereof, said intermittent transmission gear having a driving shaft and having a driven gear which is stopped while the driving shaft rotates $\frac{2}{3}$ of a turn and rotates 1/6 of a turn while the driving shaft rotates the remaining $\frac{1}{3}$ turn, said intermittent transmission gear driving shaft being connected to said motor and having said barrel cam connected thereto at a rotational ratio of 2:1, said 1/6 turn of said driven gear being carried out as the remaining $\frac{1}{3}$ turn of said driving shaft is completed at the end of the reciprocating travel of said movable frame, said worm gear having 60 teeth, and said worm having a single thread, whereby said disc is rotated through only 1° for each 1/6 turn of said driven shaft.

7. A scanning apparatus according to claim 1, in which said means for blocking rotation of said worm gear is a further worm and a secondary motor connected to said further worm, said secondary motor having a normally actuated brake, whereby when said brake is released said rotating disc can be reversely rotated by driving said further worm by said secondary motor for rotation of said worm gear.

8. A scanning apparatus according to claim 1, further comprising timing belts connecting said motor, intermittent transmission gear, barrel cam and worm.

* * * * *